(12) United States Patent
Wang et al.

(10) Patent No.: US 10,011,567 B1
(45) Date of Patent: Jul. 3, 2018

(54) METHOD FOR THE SYNTHESIS OF ACRYLATE DERIVATIVES

(71) Applicant: INNOSCI LLC, Berkeley Heights, NJ (US)

(72) Inventors: Mingwen Wang, Berkeley Heights, NJ (US); Yue Zhang, Millburn, NJ (US)

(73) Assignee: INNOSCI LLC, Berkeley Heights, NJ (US)

( * ) Notice: Subject to any disclaimer, the term of this patent is extended or adjusted under 35 U.S.C. 154(b) by 0 days.

(21) Appl. No.: 15/454,414

(22) Filed: Mar. 9, 2017

(51) Int. Cl.
*C07D 213/04* (2006.01)

(52) U.S. Cl.
CPC .................................. *C07D 213/04* (2013.01)

(58) Field of Classification Search
None
See application file for complete search history.

(56) References Cited

PUBLICATIONS

Müller et al, Biomaterials, vol. 30, pp. 4921-4929 (2009).*

* cited by examiner

*Primary Examiner* — Zinna Northington Davis
(74) *Attorney, Agent, or Firm* — Fox Rothschild LLP

(57) ABSTRACT

The present invention provides an improved synthesis of a salt of acrylate derivatives. The synthesis generally includes the preparation of an ester or an amide containing a leaving group followed by the formation of a salt.

20 Claims, No Drawings

METHOD FOR THE SYNTHESIS OF ACRYLATE DERIVATIVES

FIELD OF THE INVENTION

The present invention relates to an efficient high yield synthesis of acrylate derivatives. The synthesis generally includes coupling reaction between an activated carbonyl-containing compound and an alcohol followed by salt formation.

BACKGROUND TO THE INVENTION

The monomer of 12-methacryloyloxydodecylpyridinium bromide (MDPB) has been widely used in the field of dentistry due to its antibacterial activity. The synthesis of MDPB reported so far generally involves the formation of a pyridinium salt which is then coupled with an acid chloride to provide the target compound. The yield and purity of the product may vary depending on the specific reaction conditions.

A need exists for an improved method which is suitable for the synthesis of various acrylates and derivatives. In particular, the method should be amenable to large scale production as well as lab research.

SUMMARY OF THE INVENTION

The present invention met such a need. The method disclosed herein allows for an efficient synthesis of quaternary salts of various acrylates in high yield and high purity. In particular, the method can be employed in large scale synthesis with significantly lower cost than previously reported methods. The procedure for purifying the product and recycling the reagent also makes the method environmentally friendly.

The method generally includes reacting Intermediate A with M to form a salt of Formula I.

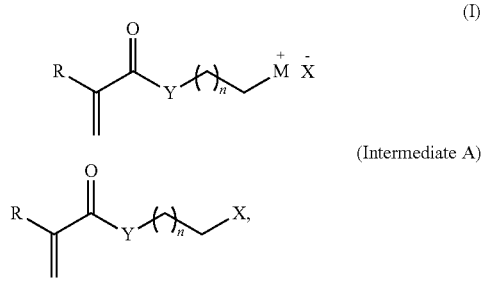

(Intermediate A)

R is H or a $C_{1-6}$alkyl. M is a tertiary amine, a triaryl phosphine, or a heteroaryl. The heteroaryl contains a lone electron pair capable of being protonated. The lone electron pair does not participate in the conjugated aromaticity system in order for it to be available for protonation. X is a Cl, Br, or I. Y is oxygen or nitrogen substituted with H, $C_{1-6}$alkyl or an aryl. n is an integer between 1 and 16, inclusive.

Intermediate A can be prepared by coupling an activated acrylate or acryloyl halide with an alcohol. The addition sequence of the reactants in the coupling step is important for a high yield reaction.

DETAILED DESCRIPTION OF THE INVENTION

The present invention relates to a new method of synthesizing acrylate derivatives. In comparison with conventional approaches where one or more side products often interfere with the purification of the final product and compromise the reaction yield and the purity of the product, the present invention provides an efficient synthesis with excellent purity and yield. The method can be adapted to acrylates and derivatives with various substitution patterns. In order to more clearly and concisely describe the subject matter of the claims, the following definitions are intended to provide guidance as to the meaning of terms used herein.

As used herein, the articles "a" and "an" as used herein mean "one or more" or "at least one," unless otherwise indicated. That is, reference to any element of the present invention by the indefinite article "a" or "an" does not exclude the possibility that more than one of the element is present.

As used herein, the term "about" means the referenced numeric indication plus or minus 10% of that referenced numeric indication.

As used herein, the term "alkyl," include straight- and branched-chain and cyclic monovalent substituents. Examples include methyl, ethyl, propyl, isopropyl, and cyclopropyl. Where indicated, a C1-C16 alkyl or $C_{1-16}$alkyl substituent may contain any number of carbons between 1 and 16. Likewise, a C1-C6 alkyl substituent may contain 1, 2, 3, 4, 5, or 6 carbons. The term C1-C6 alkyl is used interchangeably with $C_{1-6}$alkyl.

As used herein, the term "aryl" refers to optionally-substituted monocyclic and fused bicyclic hydrocarbyl moiety. Any monocyclic or fused ring bicyclic system which has the characteristics of aromaticity in terms of electron distribution throughout the ring system is included in this definition. Typically, the ring systems contain 5-12 ring member atoms.

As used herein, the term "heteroaryl" refers to optionally-substituted aromatic monocyclic and fused bicyclic heterocycles containing one or more N atom. The inclusion of a heteroatom permits inclusion of 5-membered rings as well as 6-membered rings. Heteroaryls containing a lone electron pair on nitrogen capable of being protonated include, for example, optionally substituted pyridine and imidazole.

Disclosed herein is a method of making a compound of Formula I.

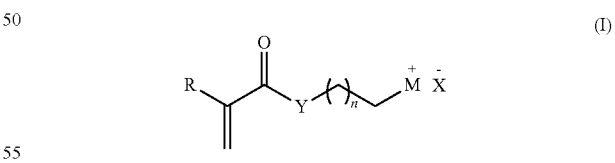

R is H or a $C_{1-6}$alkyl. In some embodiments, R is H. In some embodiment, R is methyl. M is a tertiary amine, a triaryl phosphine or a heteroaryl. In some embodiments, M is a tertiary amine which can be a cyclic or non-cyclic amine. Non-limiting examples include N-methylmorpholine, trimethylamine, diethylamine, N-alkylpiperidine, and N-alkylmorpholine, In some embodiment, M is heteroaryl which contains a nitrogen having a lone electron pair capable of being protonated. In some embodiments, the heteroaryl is optionally substituted pyridine, or imidazole. The heteroaryl can have one, two or three substituents such as $C_{1-6}$alkyl, halogen, hydroxyl, $C_{2-4}$alkynyl, $(CH_2)_nCF_3$, $OCHF_2$, $OCF_3$, $C_{3-6}$ cycloalkyl, $O(CH_2)_nC_{3-6}$ cycloalkyl, amide, reverse amide, ester, ketone, $NO_2$, CN, amino, sulfonate, sulfonamide, ether, $C_{5-10}$ heterocyclyl, $C_{6-10}$ aryl, $OC_{6-10}$ aryl, and $OC_{5-10}$ heterocyclyl. Heterocyclyl includes heteroaryl and non-aromatic rings containing one or more heteroatoms. Non-limiting examples of substituted pyridines include para-dimethylamino pyridine, 2-fluoropyridine, 3-fluoropyridine, 4-fluoropyridine, 4-(trifluoromethyl)pyridine, 3-(trifluoromethyl)pyridine, 2-(trifluoromethyl)pyridine, 4-methylpyridine, 3-methylpyridine, 2-methylpyridine, 3,4-dimethylpyridine, 2,4-dimethylpyridine, 2,3-dimethylpyridine, 2,5-dimethylpyridine, 2,6-dimethylpyridine, perfluoropyridine, 2-Methoxypyridine, 3-Methoxypyridine, and 4-Methoxypyridine. In some embodiments, M is a triaryl phosphine. Examples of aryl groups include phenyl, tolyl, and naphthyl.

X is a leaving group which includes for example trifluoromethanesulfonate (OTf), p-toluenesulfonate (OTS), methanesulfonate (MsO) and a halogen which can be chlorine, bromine, or Iodine. In some embodiments, X is chlorine. In some embodiments, X is bromine.

Y is oxygen or NR' wherein R' is hydrogen, $C_{1-6}$ alkyl or an aryl. In some embodiments, Y is NH. In some embodiments, Y is $NC_{1-6}$alkyl.

The integer n is any number between 1 and 16 such as 1, 2, 3, 4, 5, 6, 7, 8, 9, 10, 11, 12, 13, 14, 15, and 16. In some embodiments, n is 11, R is H or methyl, M is pyridine, and X is bromine.

The synthesis of compound of Formula I includes reacting Intermediate A with M. Various conditions such as heating or microwave radiation can be employed to promote the reaction. In some embodiments, the temperature of the reaction is controlled at lower than about 50° C., lower than about 45° C., lower than about 40° C., lower than about 30° C., lower than about 20° C. In some embodiments, the reaction temperature is controlled at between about 20° C. and about 45° C. The reaction yield from Intermediate A and M to the target product is generally above about 60%, above about 70%, above about 80%, above about 85%, above about 90%, or above about 95%.

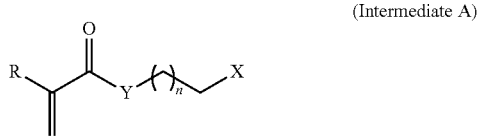

(Intermediate A)

In some embodiments, M is pyridine which can be substituted or non-substituted. In some embodiments, more than about 50%, more than about 60%, more than about 70%, more than about 80%, more than about 90%, more than about 95% or more than about 99% of the reaction mixture by weight are Intermediate A and M. In some embodiments, the reaction mixture consists of Intermediate A and M and is substantially free from other agents or solvents. In some embodiments, M is unsubstituted pyridine.

In some embodiments, the reaction between Intermediate A and M requires M to be in an excess by more than about 10%, more than about 20%, more than about 30%, more than about 40%, more than about 50%, more than about 60% or more than about 80%.

In reactions where no additional solvent is present, pyridine serves as a reactant as well as a solvent. At the end of the reaction, the excess pyridine can be removed by, for example, evaporation under reduced pressure. To avoid or minimize the formation of undesirable side products, the removal of pyridine needs to be performed at a temperature of less than about 45° C. in some embodiments, the temperature for pyridine removal is controlled at less than about 35° C.

The method of the present invention can further include a step for the preparation of Intermediate A, which is synthesized through the coupling reaction between an activated carbonyl-containing Intermediate B and a hydroxyl-containing Intermediate C or an amino-containing Intermediate C'. In Intermediate C', R' is H, $C_{1-6}$alkyl or an aryl.

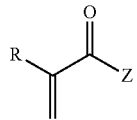

(Intermediate B)

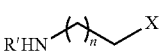

(Intermediate C)

(Intermediate C')

Intermediate B with an activated or reactive carbonyl includes for example an acid halide, an acid anhydride, and an ester. Z is a group activating the carbonyl and non-limiting examples include carboxy, succinimide, and halide. In some embodiments, the activated carbonyl is an acid halide, wherein the halide can be chloride or bromide (Z). It is noted that Intermediate B can be an ester where Z is Oalkyl or Oaryl.

To prepare Intermediate A, Intermediate B is generally added to a solution of Intermediate C or C' where the temperatures is controlled below 20° C. in some embodiments, the temperatures ranges from about −10° C. to about 20° C. or from about −10° C. to about 0° C.

The reaction between Intermediate B and Intermediate C or Intermediate C' generally proceeds in the presence of a base. Non-limiting examples of the base include trimethylamine, diisopropylethylamine, and pyridine. In some embodiments, the base is trimethylamine.

The coupling reaction between Intermediate B and Intermediate C' can also employ various methods known in peptide chemistry. The reaction condition for amide formation can be determined by one of ordinary skill in the art without undue experiments.

The mixing of Intermediate B and Intermediate C or Intermediate C' generally proceeds at a temperature of less than about 10° C. To minimize the formation of side products, the temperature can be lowered to less than about 5° C., less than about 0° C., less than about −5° C., or less than about −10° C. In some embodiments, the temperature is controlled between about −20° C. and about 20° C., between about −20° C. and about 10° C., between about −20° C. and about 0° C., or between about −10° C. and about 0° C.

The base is preferably added after the mixing of Intermediate B and Intermediate C or Intermediate C'. In some cases where the base is added substantially before the mixing of Intermediate B and Intermediate C or Intermediate C', the formation of undesirable side products are observed. Therefore, in some embodiments, Intermediate B is initially mixed with Intermediate C or Intermediate C' in the absence of a base. The base is then added substantially after the mixing of Intermediate B and Intermediate C or Intermediate C'. In order to further minimize the formation of the side product, the temperature during the addition of the base and/or after the addition is controlled at below about 10° C., below about 6° C., below about 4° C., below about 2° C., or below about 0° C.

An exemplary synthesis for MDPB is illustrated below. The sequence includes an ester synthesis step and a salt formation step.

Ester Synthesis:

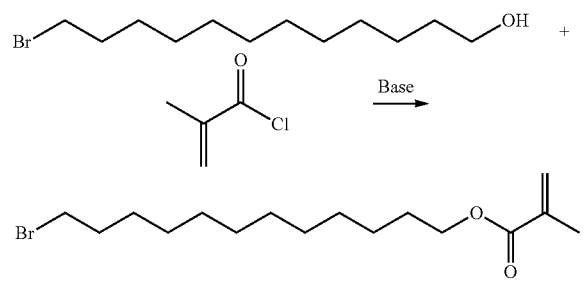

Salt Formation:

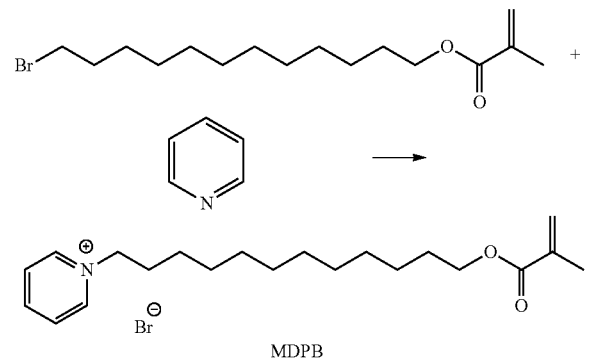

The ester synthesis step preferably mixes the alcohol and acid chloride prior to the addition of the base in order to avoid the formation of side products. Triethylamine works best as a base whereas di-isoproylethyl amine fails to provide any decent amount of product. The reaction is less efficient in pyridine than in triethyl amine in terms of the product yield and the reaction rate. The ester synthesis step also preferably proceeds at a temperature below about 5° C. to effectively minimize the formation of side products. In some embodiments, the temperature is controlled between about 0° C. to about 5° C.

After the completion of the salt formation, pyridine can be readily removed, for example, on an equipment such as a rotavap. However, the temperature is preferably controlled at a certain range to prevent MDPB from polymerizing. MDPB has been observed to partially polymerize at a temperature above 45° C. In some embodiments, the temperature for pyridine removal is controlled at about 10° C. to about 35° C.

Upon the completion of the reaction between Intermediate B and Intermediate C, various procedures can be used to isolate and/or purify Intermediate A. In some embodiments, an alcohol such as methanol is added after the reaction is completed. In some embodiments, the purification of the reaction can be accomplished by passing the crude product through a pad of silica gel. In some embodiments, the purification of final product can be accomplished with recrystallization. A preferred solvent used in recrystallization is methyl tertiary-butyl ether.

The method of the present invention is suitable for not only lab scale synthesis, but also large scale production. The scale of the production can be higher than 5 kg, higher than 50 kg, higher than 500 kg, and higher than 20000 kg.

The combined yield for the preparation of Intermediate A and final product is generally above about 50%, above about 60%, above about 70%, above about 80%, above about 85%, above about 90%, or above about 95%.

Example

The following example illustrates the synthesis of 12-methacryloyloxydodecylpyridinium bromide (MDPB).

To a 3-necked 5 L-glass reactor equipped with J-Kem temperature controller/monitor was added 12-bromododecan-1-ol (500 g, 1.885 mole) and dichlormethane (3 L) at room temperature. The above mixture was stirred by magnetic stirrer at room temperature for 10 minutes. The reaction mixture was cooled down to between −10° C. and 0° C. under dry ice/acetone bath, and Mmethacryloyl chloride (B) (246 g, 2.356 mole) was added in one portion, keeping the temperature at −10° C.-0° C. stirring for 10 minutes. To the above reaction mixture was then added dropwise triethylamine (238 g, 2.356 mole) via liquid addition funnel. The temperature of the reaction mixture was kept below 4° C. until TLC showed no more starting material. To the above reaction mixture was then added MeOH (30 ml) and followed by aq. HCl (0.15N, 1.5 L) to adjust the pH to about 2. The two phases were separated and the aqueous phase was extracted with dichlormethane (1×3 L). The combined organic phases were washed with brine(1×1 L) and concentrated and passed through a pad of silica gel and then concentrated again to give 520 g of pale yellow oil (Intermediate A), which was directly used in the next step.

To a 2-L glass reactor was added 520 g of Intermediate A and Pyridine (740 g) at room temperature. The reaction mixture was heated to 45° C. and stirred at this temperature for 26 hours. The reaction mixture was cooled down to room temperature and concentrated to remove most of excess pyridine under reduced pressure on Rota vapor at 20° C.-35° C. to give 580 g of crude MDPB as sticky oil.

To the above 580 g of crude MDPB was added Methyl Tertiary Butyl Ether (1.2 L). The mixture was stirred at room temperature for 1 hour under nitrogen protection. The reactor of the mixture was placed in an ice/water bath for 4 hour. Solid product was observed. A small amount of pure solid MDPB can be used as a seed to promote crystal formation. The solid was collected via filtration using glass filtration funnel and washed with Methyl Tertiary Butyl Ether (3×1 L) at room temperature. The solid was put in a 1-necked glassware under high vacuum pump for 16 hours to give 490 g of pure MDPB, as a white solid, with purity (99%, by HPLC) and overall yield (63%).

HPLC gradient method: mobile phases: 60% of Water, 40% of ACN, flow rate 0.6 ml/min HNMR (CDCl3), 1.20-1.41 (m, 16H), 1.60-1.73 (m, 2H), 1.92-2.11 (m, 5H), 4.15 (m, 2H), 5.05 (m, 2H), 5.48 (m, 1H), 6.12 (m, 1H), 8.13 (m, 2H), 8.50 (m, 1H), 9.50 (m, 2H)

It will be understood by those of skill in the art that numerous and various modifications can be made without departing from the spirit of the present invention. Therefore, it should be understood that the various embodiments of the present invention described herein are illustrative only and not intended to limit the scope of the present invention.

The invention claimed is:

1. A method of synthesizing the compound of Formula I,

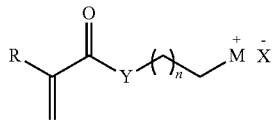
(I)

comprising
(a) reacting an activated carbonyl-containing Intermediate B with a hydroxyl-containing Intermediate C in the presence of a base to provide Intermediate A,

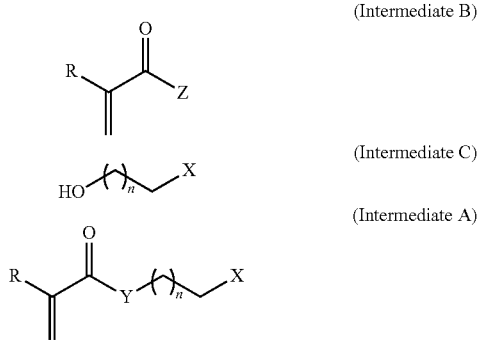

(Intermediate B)

(Intermediate C)

(Intermediate A)

wherein
R is H or a C1-C6 alkyl;
X is a Cl, Br, I;
Y is O;
Z is a carbonyl-activating group, and R' is H, $C_{1-6}$ alkyl or an aryl;
n is an integer between 7 and 15, inclusive; and
(b) reacting the Intermediate A with M, wherein
M is a tertiary amine or is selected from the group consisting of pyridine, para-dimethylamino pyridine, 2-fluoropyridine, 3-fluoropyridine, 4-fluoropyridine, 4-(trifluoromethyl)pyridine, 3-(trifluoromethyl)pyridine, 2-(trifluoromethyl)pyridine, 4-methylpyridine, 3-methylpyridine, 2-methylpyridine, 3,4-dimethylpyridine, 2,4-dimethylpyridine, 2,3-dimethylpyridine, 2,5-dimethylpyridine, 2,6-dimethylpyridine, perfluoropyridine, 2-Methoxypyridine, 3-Methoxypyridine, 4-Methoxypyridine, and N-methylmorpholine.

2. The method of claim 1, wherein R is H or methyl.

3. The method of claim 1, wherein M is selected from the group consisting of pyridine, para-dimethylamino pyridine, 2-fluoropyridine, 3-fluoropyridine, 4-fluoropyridine, 4-(trifluoromethyl)pyridine, 3-(trifluoromethyl)pyridine, 2-(trifluoromethyl)pyridine, 4-methylpyridine, 3-methylpyridine, 2-methylpyridine, 3,4-dimethylpyridine, 2,4-dimethylpyridine, 2,3-dimethylpyridine, 2,5-dimethylpyridine, 2,6-dimethylpyridine, perfluoropyridine, 2-Methoxypyridine, 3-Methoxypyridine, 4-Methoxypyridine, and N-methylmorpholine.

4. The method of claim 1, wherein X is Cl.

5. The method of claim 1, wherein X is Br.

6. The method of claim 1, wherein the Intermediate A and M react at a temperature between about 20° C. and about 60° C.

7. The method of claim 1, wherein the Intermediate A and M react in a mixture containing less than about 50% of other agent or solvent by weight.

8. The method of claim 1, wherein M is pyridine, and wherein the Intermediate A and M react in a mixture substantially free from any other agent or solvent.

9. The method of claim 8, further comprising removing excess pyridine under a temperature of less than about 50° C.

10. The method of claim 8, further comprising removing excess pyridine under a temperature of less than about 35° C.

11. The method of claim 1, wherein the base is added only after the Intermediate B is mixed with the Intermediate C.

12. The method of claim 1, wherein the base is selected from the group consisting of triethylamine, diisopropylethylamine, and pyridine.

13. The method of claim 1, wherein the Intermediate B reacts with the Intermediate C under a temperature of lower than about 5° C.

14. The method of claim 1, wherein Z is Cl, further wherein the compound of Formula I is obtained in a combined yield of above about 50% from Intermediate C.

15. The method of claim 1, further comprising purifying the compound of Formula I by recrystallization in methyl tertiary butyl ether.

16. The method of claim 1, wherein Z is Cl.

17. The method of claim 1, wherein the base is triethylamine.

18. A method of synthesizing the compound of Formula I,

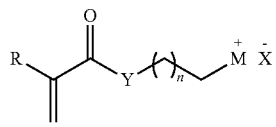
(I)

comprising
(a) reacting an activated carbonyl-containing Intermediate B with a hydroxyl-containing Intermediate C in the presence of a base selected from the group consisting of triethylamine, diisopropylethylamine, and pyridine to provide Intermediate A,

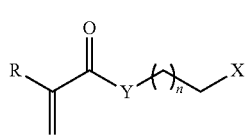
(Intermediate A)

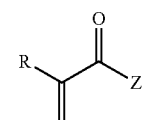
(Intermediate B)

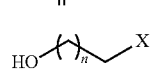
(Intermediate C)

wherein
R is H or a C1-C6 alkyl;
X is a Cl, Br, I, trifluorosulfonate (OTf), methylsulfonate (OMs) or toylysulfonate (OTs);

Y is O;

Z is a carbonyl-activating group, and R' is H, C1-6alkyl or an aryl;

n is an integer between 1 and 16, inclusive; and (b) reacting the Intermediate A with M, wherein M is a tertiary amine or is selected from the group consisting of pyridine, para-dimethylamino pyridine, 2-fluoropyridine, 3-fluoropyridine, 4-fluoropyridine, 4-(trifluoromethyl)pyridine, 3-(trifluoromethyl)pyridine, 2-(trifluoromethyl)pyridine, 4-methylpyridine, 3-methylpyridine, 2-methylpyridine, 3,4-dimethylpyridine, 2,4-dimethylpyridine, 2,3-dimethylpyridine, 2,5-dimethylpyridine, 2,6-dimethylpyridine, perfluoropyridine, 2-Methoxypyridine, 3-Methoxypyridine, 4-Methoxypyridine, and N-methylmorpholine.

19. The method of claim 18, wherein the base is added only after the Intermediate B is mixed with the Intermediate C.

20. The method of claim 18, wherein the base is triethylamine.

\* \* \* \* \*